United States Patent [19]

Gorka et al.

[11] 4,379,840

[45] Apr. 12, 1983

[54] QUANTITATIVE ANALYSIS OF URIC ACID

[75] Inventors: Günther Gorka, Wiesbaden-Auringen; Klaus Stinshoff, Munich, both of Fed. Rep. of Germany

[73] Assignee: C. H. Boehringer Sohn, Ingelheim am Rhein, Fed. Rep. of Germany

[21] Appl. No.: 278,677

[22] Filed: Jun. 29, 1981

[30] Foreign Application Priority Data

Jul. 3, 1980 [DE] Fed. Rep. of Germany ....... 3025170

[51] Int. Cl.³ .................. C12N 9/04; C12N 9/96; C12Q 1/30; C12Q 1/32
[52] U.S. Cl. ...................... 435/10; 435/26; 435/27; 435/188; 435/190; 435/810
[58] Field of Search .............. 435/10, 26, 27, 188, 435/190, 810

[56] References Cited

U.S. PATENT DOCUMENTS 3,746,625 7/1973 Bergmeyer et al. ............. 435/26
3,956,069 5/1976 Allain et al. ..................... 435/14
4,189,536 2/1980 Green ............................. 435/14
4,202,938 5/1980 Haeckel et al. .................. 435/10
4,247,630 1/1981 Ziegenhorn et al. ............. 435/10

OTHER PUBLICATIONS

Black, Arch. Biochem. Biophys., 34, 86–97 (1951).
Steinman et al., J. Biol. Chem., 242(21), 5019–5023 (1967).
Bartl et al., Clin. Chem., 25(4), 619–621 (1979).

Primary Examiner—Esther M. Kepplinger
Attorney, Agent, or Firm—Hammond & Littell, Weissenberger and Muserlian

[57] ABSTRACT

This invention relates to a process for determining the uric acid content of biological material by contacting the biological material with a reagent composition comprised of uricase, catalase, aldehyde dehydrogenase, a lower alkanol, and nicotinamide adenine dinucleotide or nicotinamide adenine dinucleotied phosphate, the improvement which comprises determining the uric acid content in the presence of 2-mercaptosuccinic acid.

6 Claims, 2 Drawing Figures

QUANTITATIVE ANALYSIS OF URIC ACID

FIELD OF THE INVENTION

This invention is directed to the quantitative analysis of uric acid. More specifically, this invention is directed to the quantitative analysis of uric acid in biological material wherein 2-mercaptosuccinic acid is used as a reagent.

BACKGROUND OF THE INVENTION

The quantitative analysis of uric acid in a biological substance such as serum or plasma is a test which has to be carried out frequently and therefore plays an important part of clinical chemistry.

Previously, the enzymatic determination of uric acid has predominantly been carried out using the uricase method, which is used as a reference method, and by the method of Kageyama [Clin. Chim. Acta 31, 421 (1971)]. [See, also, Bergmeyer, "Methoden der enzymatischen Analyse", Volume 2, (1974), 1999–2005, Verlag Chemie)]. However, both methods have a number of disadvantages: In the uricase method, the high intrinsic absorbance of the serum sample at 293 nm is accompanied by a relatively low signal, due to the reduction in uric acid. Moreover, the procedure uses a wavelength for which the average laboratory does not have suitable equipment.

According to the Kageyama process, the $H_2O_2$ formed by the action of the uricase is used for the oxidation of methanol to formaldehyde. The formaldehyde reacts with acetylacetone and ammonia, 3,5-diacetyl-1,4-dihydrolutidine being formed. However, at the end of the reaction a period of 60 minutes at elevated temperature (37° C.) is required, and this is a major disadvantage when automatic analyzers are used.

Recently a process has become known [German Published Application (DE-OS) No. 24 50 726] wherein the $H_2O_2$ formed is determined using catalase and aldehyde dehydrogenase, while NAD(P)H, which forms from NAD(P), can be measured photometrically at 334, 340, or 366 nm. This process has proven to be advantageous, as compared with processes used previously, particularly for determining uric acid content, since it takes only 15 minutes rather than 60 minutes, as in the past (Bergmeyer H. U., supra, pages 2002–2005). Consequently, this method is particularly suitable for automatic analyzers.

When this latest process was used, it was found that the serum contained constituents which deactivated the aldehyde dehydrogenase. Thus, it was found that after incubation of the serum with reagent and without uricase for 4 minutes and subsequent addition of uricase, the reaction is finished after about 10 minutes. If the serum is pre-incubated for 30 minutes, the reaction often does not come to an end until 20 to 30 minutes after the addition of uricase or else it continues as a creeping reaction (change in absorptions, $\Delta A$, per minute) lasting a considerable time. An additional problem is that the decrease in the aldehyde dehydrogenase activity occurs at different speeds in different sera.

This is a major disadvantage, particularly when the reagent is used in automatic analyzers. Longer pre-incubation periods are often required, because of the nature of the apparatus, before uricase is added as the starter reagent. Then, as a result of the reduction in the aldehyde dehydrogenase activity, the reaction may not be completed within the specified time.

The situation described gives rise to even greater problems in automatic analyzers which analyze substrates on a kinetic basis. Since it is the speed of the reaction which is being measured in such a case, the activity of the enzymes concerned must remain constant during the measuring period. If this is not the case, the reaction speed is affected not only by the quantity of substrate present but also by the fluctuating activity of the enzymes concerned, and is thus falsified. A constant aldehyde dehydrogenase activity must be ensured, particularly in those cases when the aldehyde dehydrogenase reaction is the rate-determining step of the reaction as a whole.

It is known from the literature [Black, S. Arch. Biochem. Biophys., 34 (1951), 86–97; Steinmann, C. R., and Jacoby, W. B., J. Biol. Chem., 242 (1967), 5019–5023] that aldehyde dehydrogenase is an enzyme containing thiol groups and that it can be stabilized with thiol reagents and/or with complex-forming agents. Ethylenediaminetetraacetic acid (EDTA), cysteine, glutathione, mercapto-ethanol, and thioglycolic acid are examples of reagents useful in this regard. EDTA is not sufficiently active as a protective reagent in the presence of serum. The other reagents mentioned certainly protect aldehyde dehydrogenase; however, in the incubation mixture their use results in a creeping reaction which, dependent upon the concentration of the substance added and on the serum being investigated, is from about 0.001 and 0.010 absorptions/minute. Representative values are set forth in the following table:

TABLE

| Additive | Concentration (mol/liter) | Creeping reaction ($\Delta A$/min) |
|---|---|---|
| Dithiothreitol | $5 \times 10^{-4}$ | 0.002–0.003 |
| Cysteine | $5 \times 10^{-4}$ | 0.005–0.007 |
| Glutathione | $5 \times 10^{-4}$ | 0.004–0.007 |
| Thioglycolic acid | $5 \times 10^{-4}$ | 0.001–0.002 |

DETAILED DESCRIPTION OF THE INVENTION

Figure 1:
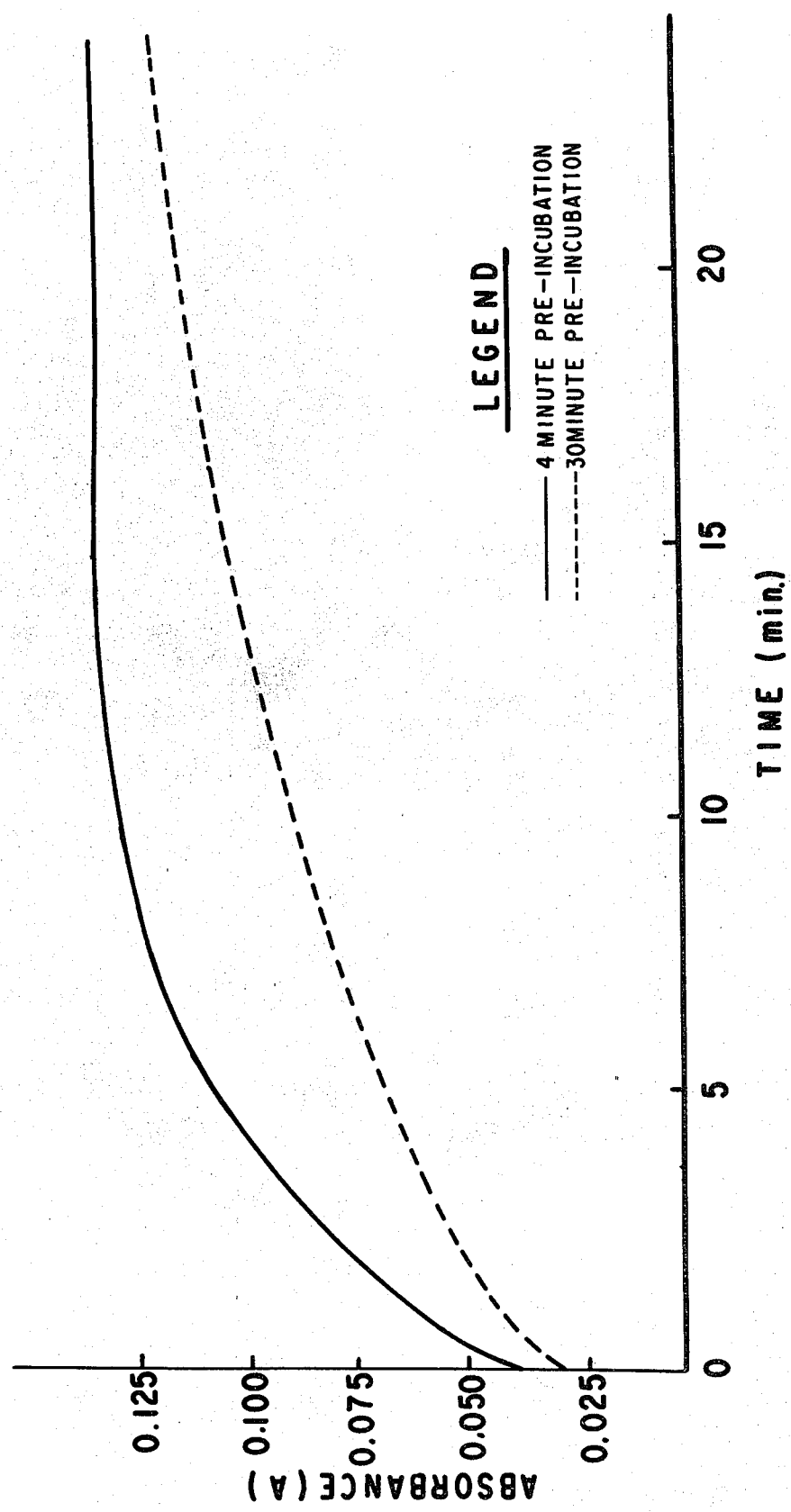
FIG. 1 is a graphical representation of absorbency versus time for a known reagent composition.

It has now been found that in the quantitative analysis of uric acid in biological media or materials, aldehyde dehydrogenase is protected by the addition of 2-mercaptosuccinic acid and, in contrast to cases where other thiol reagents are used, no creeping reaction occurs. By the addition of this reagent, it is now possible to carry out aldehyde dehydrogenase-dependent reactions without any difficulty, either in automatic analyzers or manually. Moreover, with longer pre-incubation times, the time taken to reach the end point is not increased, in contrast to the known processes.

The substances specified in German Published Application (DE-AS) No. 27 18 588 for preventing creeping reactions are concerned predominantly with uraemic samples in which certain enzymes may occur with increased activity levels. Their influence is suppressed by the addition of substances mentioned in German Published Application (DE-AS) No. 27 18 588 [see, Clin. Chem 25/4, 619–621 (1979)]. These substances do not provide any protection for the aldehyde dehydrogenase.

In contrast, according to the invention herein 2-mercaptosuccinic acid protects the aldehyde dehydrogenase, which is critical in detecting the uric acid reaction, from deactivating substances which are present in any serum, without having to make allowances for a creeping reaction of varying degrees of intensity. It therefore differs substantially from the substances specified in German Published Application (DE-AS) No. 27 18 588 both in its place of action and in the activity itself.

In quantitatively determining the uric acid content of biological material, such as serum or plasma, the biological material is contacted with a sufficient amount of reagent composition, preferably from about a 10 to 1000-fold quantity, of reagent composition based on the volume of biological material. In a preferred embodiment, the biological material is contacted first with a composition comprising buffer solution, an alcohol such as a lower alkanol, NAD+ (nicotinamide adenine dinucleotide) or NADP+ (nicotinamide adenine dinucleotide phosphate), catalase, aldehyde dehydrogenase, 2-mercaptosuccinic acid, and, optionally, oxamic acid, and then with a sufficient amount of uricase. In this embodiment the reagent composition with which the biological material is contacted is thus in two separate portions.

In an especially preferred embodiment of the invention, the total reagent composition comprises from about 25 to 500 IU (International Enzyme Units)/liter of uricase, from about 300 to 1000 kIu/liter of catalase, from about 100 to 500 IU/liter of aldehyde dehydrogenase, from about 0.5 to 2 mol/liter of ethanol, from about 0.2 to 1.5 mmol/liter of NAD+ or NADP+, from about 0.01 to 0.5 mol/liter of oxamic acid, from about 20 to 100 mmol/liter of buffer solution, and from about 0.0001 to 0.1 mol/liter of 2-mercaptosuccinic acid, the pH of the composition being from about 6.5 to 9.

The following example is intended to illustrate the invention and should not be construed as limiting the invention thereto.

EXAMPLE

| Reagent 1: | |
|---|---|
| Potassium dihydrogen phosphate buffer | 42 mmol/liter, pH 8.0 |
| Ethanol | 1.43 mmol/liter |
| NADP+ | 0.265 mmol/liter |
| Catalase | 350 kIU/liter |
| Aldehyde dehydrogenase | 250 IU/liter |
| 2-Mercaptosuccinic acid | none or from 1 to 5 mmol/liter |
| Reagent 2: | |
| Uricase | 5 kIU/liter |

Determining uric acid concentration:

Measuring radiation: 334 nm, 340 nm, 365 nm; layer thickness: 1 cm; temperature: 25° C.

One milliliter of Reagent 1 is pipetted into a bath, 50 μl of a biological sample is added, and the components are mixed by stirring. The absorbance is recorded on a graph recorder, the value $A_1$ being read after a specific pre-incubation period (for example, about 4 minutes), and then 10 μl of Reagent 2 are added, the value $A_2$ being read off after 15 minutes.

Calculating the concentration (c) of uric acid:
$C = (A_2 - A_1) \times 3.43$ mmol/l (Hg 334 nm)
$C = (A_2 - A_1) \times 3.36$ mmol/l (Hg 340 nm)
$C = (A_2 - A_1) \times 6.06$ mmol/l (Hg 365 nm, NADP)

Test 1

Figure 2:
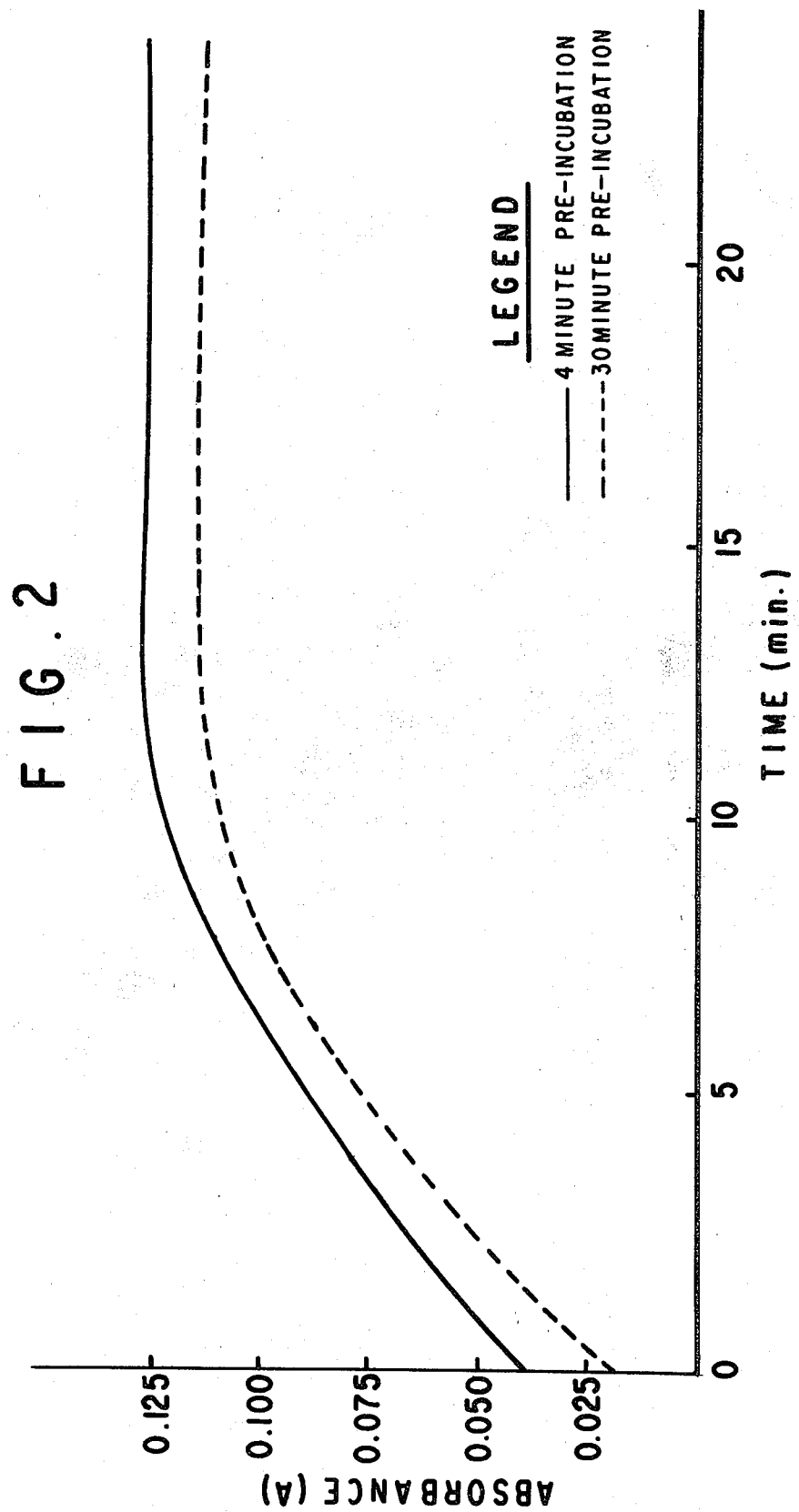
FIG. 2 is a graphical representation of absorbency versus time for a reagent composition according to the invention.

With various sera, various pre-incubation periods were tried, using Reagent 1, before the addition of Reagent 2. The results are represented graphically in FIGS. 1 and 2. In FIG. 1 two similar runs where no 2-mercaptosuccinic acid was present in Reagent 1 had pre-incubation periods of 4 minutes and 30 minutes, respectively. In FIG. 2, two similar runs where 5 mmol/l of 2-mercaptosuccinic acid were present in Reagent 1 also had pre-incubation periods of 4 minutes and 30 minutes, repectively. It can be seen that the time taken to reach the end point with the longer preincubation periods is not significantly longer than the shorter pre-incubation period.

Test 2

A test of stability on storage both at room temperature and at refrigerator temperature was carried out with reagents having the above compositions, that is, with or without 2-mercaptosuccinic acid. The criterion adopted was the time taken to reach the end point in the determination of uric acid. If this time was more than 15 minutes, the reagent was classed as no longer being useable.

The shelf life is at least 7 days at room temperature and at least 14 days at refrigerator temperature when from about 1 to 5 mmol of 2-mercaptosuccinic acid are present in the reagent composition. This shelf life is significantly longer than that obtained for a reagent composition without 2-mercaptosuccinic acid, namely, 1 day at room temperature and 8 days at refrigerator temperature.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. In a process for determining the uric acid content of biological material by contacting the biological material with a reagent composition containing uricase, catalase, aldehyde dehydrogenase, a lower alkanol, and nicotinamide adenine dinucleotide or nicotinamide adenine dinucleotide phosphate, the improvement which comprises contacting the biological material with a reagent composition comprising:
(a) from about 25 to 500 IU/liter of uricase;
(b) from about 300 to 1000 kIU/liter of catalase;
(c) from about 100 to 500 IU/liter of aldehyde dehydrogenase;
(d) from about 0.5 to 2 mol/liter of ethanol;
(e) from about 0.2 to 1.5 mmol/liter of NAD+ or NADP+;
(f) from about 20 to 100 mmol/liter of buffer; and
(g) from about 0.0001 to 0.1 mol/liter of 2-mercaptosuccinic acid.

2. The process according to claim 1, wherein the process is carried out at a pH value of from about 6.5 to 9.

3. The process according to claim 2, wherein the process is carried out at a pH value of from about 8 to 8.5.

4. A reagent composition for determining the content of uric acid in biological material which comprises:
   (a) from about 25 to 500 IU/liter of uricase;
   (b) from about 300 to 1000 kIU/liter of catalase;
   (c) from about 100 to 500 IU/liter of aldehyde dehydrogenase;
   (d) from about 0.5 to 2 mol/liter of ethanol;
   (e) from about 0.2 to 1.5 mmol/liter of $NAD^+$ or $NADP^+$;
   (f) from about 20 to 100 mmol/liter of buffer; and
   (g) from about 0.0001 to 0.1 mol/liter of 2-mercaptosuccinic acid.

5. The reagent composition of claim 4 which also contains from about 0.01 to 0.5 mol/liter of oxamic acid.

6. The reagent composition of claim 5 which has a pH of from about 6.5 to 9.

* * * * *